United States Patent [19]
Brittain

[11] Patent Number: 5,981,698
[45] Date of Patent: Nov. 9, 1999

[54] ANTIMICROBIAL POLYPEPTIDES

[75] Inventor: Andrew Marsh Brittain, Huntsville, Ala.

[73] Assignee: CyberChemics, Inc., Huntsville, Ala.

[21] Appl. No.: 08/909,433

[22] Filed: Jun. 3, 1997

[51] Int. Cl.[6] .................................................. C07K 7/00
[52] U.S. Cl. ........................ 530/326; 514/13; 424/405
[58] Field of Search ...................... 536/27; 435/252.31, 435/320.1; 514/12, 13; 530/306, 326; 424/405

[56] References Cited

U.S. PATENT DOCUMENTS 5,073,632  12/1991  Donovan .................................. 536/27

OTHER PUBLICATIONS

Widner et al., J. of Bacteriology, 965–974, (1989).

*Primary Examiner*—F. T. Moezie
*Attorney, Agent, or Firm*—Bryan Cave LLP

[57] ABSTRACT

A series of structurally diverse chemical and pharmaceutical compounds show antimicrobial activity. This new class of broad spectrum antimicrobials has been identified with molecular weight below 2600, high aqueous solubility, low cytotoxicity to mammalian cells and usefulness as preservatives, antibacterial, antifungal and food additive applications.

```
GIGTLLGKKKTKFLKNILKL   as represented in
                      ID sequence No. 1

VGSLVGKRILSELRNLI     as represented in
                      ID sequence No. 2
``` as set fourth in SEQ. I.D. No. 1, or salts thereof.

2 Claims, No Drawings

ANTIMICROBIAL POLYPEPTIDES

BACKGROUND OF THE INVENTION

A new class of broad spectrum antimicrobials has been identified with molecular weight below 2600, high aqueous solubility, low cytotoxicity to mammalian cells such as human erythrocytes and usefulness as preservatives, antibacterial, antifungal, agricultural seed coatings and food additive applications.

BACKGROUND OF THE INVENTION

The present invention describes pharmaceutically relevant compounds for use as preservatives and antimicrobial application and may be applied to treatment or prevention of manifestations of infectious disease. More specifically, the present invention includes a new class of polypeptides and their associated salts thereof, which possess broad spectrum antimicrobial potency and favorable therapeutic profiles. In addition, the application may embody a variety of chemical disinfectant uses for reduction in bacterial growth and sterilization. Applications are widespread, from antibacterial and antifungal creams, food preservatives, indwelling medical device coatings to antibiotics for human disease treatment. Polypeptides are key carriers of biochemical information in all mammalian systems, thus garnering considerable interest as therapeutic and diagnostic reagents. No such polypeptide sequences as described in the present invention have been previously discovered or isolated either synthetically using de novo design or purified from compositions in the natural ecosystems.

SUMMARY OF INVENTION

An object of the invention is to provide a novel family of antimicrobial and preservative compounds isolated and derivatized from modified fragments of insecticidal crystal proteins, specifically the *Bacillus thuringiensis* family of precursors, polypeptides and proteins. More specifically, the compound (SEQ. I.D. 1) is a small fragment of a much larger insecticide as a further part from delta-Endotoxin (insectocide), N-terminal domain from *Bacillus thuringiensis* related proteins (632 amino acids) expressed in gram positive bacteria (*Bacillus thuringiensis* (SUBSP. *kurstaki*) protein, sequence fragment 65-81, STRAIN=HD-263) as listed by amino acid in (SEQ. I.D. 2).

In 1984 more than one thousand naturally occurring microbial products were shown to be effective against insect pests, yet only fourteen were approved for commercial use in the U.S. In 1991 the penetration of the global agrochemical market by biological products was only 0.45%. The most widely used microbial pesticides are derived from the bacterium *Bacillus thuringiensis*. This bacterial agent is used to control a wide range of leaf-eating caterpillars, and mosquitos. *Bacillus thuringiensis* produces a proteinaceous paraspore or crystal which is toxic upon ingestion by a susceptible insect host. Structurally, members of the genus of bacteria, Bacillaceae, are gram-positive, with insect toxins' in membrane translocation domains. These multi-helical domains of various folds are thought to unfold in the epithelial membrane of insect larvae with various specificities and are classed as a delta-endotoxin (insectocide), N-terminal domain.

Many hundreds of strains of *Bacillus thuringiensis* (*B.t.*) produce insecticidal toxins designated as delta endotoxins. They are synthesized by sporulating *B.t.* cells. When toxin is ingested by a susceptible insect, the cells of the gut epithelium are destroyed. In their active form, this class of bacterial proteins can be highly selective for insect larvae, such as the parasporal crystal protein, *Bacillus thuringiensis* (*Bt* strain galleriae 11-67) (fragment) is wax moth-specific. This toxin is effective against the larvae of Galleria melonella (greater wax moth) but not those of Lymantria dispar (gypsy moth). As a (wettable powder) insecticide, a lethal dose of *Bt* stops insect larval feeding within the hour, resulting in death within several days. Dying larvae move slowly, discolor, then shrivel, blacken and die. The organism causes a disease in the stomach of the caterpillers and they die. It takes a very small amount of *Bt* to kill the insects, and *Bt* does not harm humans.

At a molecular level, the sequence encodes a 70 kilodalton crystal protein (delta endotoxin or crystaline entomocidal protoxin), which functionally promotes colloidosmotic lysis by binding to the midgut epithelial cells of coleoptera. The toxic segment of the protein is located in the N-terminus. The crystal protein is produced during sporulation and is accumulated both as an inclusion and as part of the spore coat.

With this background, SEQ. 1 corresponds to major structural and chemical modifications to the partial amino acid fragment of a insecticidal motif common to proteins in sporulating bacteria, *Bacillus thuringiensis*. Because these peptides can be gene-encoded, it is possible to develop and manufacture genetically engineered variants of *B.t.* bacteria with a variety of properties useful for different specific applications. In the field of manufacturing self-regulated bacterial proteins, it is known that extracellularly expressed proteins in sporulating bacteria generally, but the present domains specifically, are the first important regulators of competitive bacterial growth identified, in particular in food contamination, resistant bacterial and fungal infections. The usefulness of peptide antimicrobials have considerable promise for controlling topical infections related to abnormal cell proliferation and microbial infection.

A major problem facing microbial insecticides lies in the area of insect resistance. It was initially believed that insects would not develop resistance to microbial insecticides. Indeed, significant resistance to *Bt* was not observed during its use over more than three decades. Recently though, it has been discovered that resistance to *Bt* can evolve in the lab or field under cases of extreme selection pressure Identifying antimicrobial activity in new insecticidally related proteins is therefore a significant step toward understanding infection and cell growth.

It is further an object of the present invention to provide a novel class of antimicrobials which inhibit growth or otherwise act microbicidally in infections related to gram negative and positive bacteria, protozoa and/or parasites, fungi and the like. The minimum inhibitory concentration (MIC ug/mL) of the compounds indicate both broad spectrum and highly targeted microcidal potency.

Advantages of such compounds and other objects of invention will be apparent to those skilled in the art, as outlined in the Detailed Description of the Invention.

DETAILED DESCRIPTION OF THE INVENTION

The polypeptides discovered and described herein comprise a novel class of preservative and antimicrobial having a molecular weight less than 2600, aqueous solubility at neutral pH of approximately 100 times or more than their 50% inhibitory concentration, and non-cytotoxicity in various physiological media and sera.

Once specified as an amino acid sequence and its derivatized salts or fluorogenic chemicals, these compounds can be readily synthesized using techniques and chemical steps known to the art, such as commercially standard solid phase synthesis, solution phase synthesis, and peptides stepwise sequenced onto, for example, a polyethylene or similarly coated bead, bandage, patch or prosthetic device. In accordance with the present invention, the antimicrobial peptides may be prepared by, for example, a first method, i.e. solid phase method employing an Fmoc amino acid (Sheppard, R. C. et al. J. Chem. Soc. Chem. Comm. 165–166, 1985). The second method for synthesizing the antimicrobial peptides of the present invention is a solid phase method employing the Boc-amino acid according to Merrifield, J. Am. Chem. Soc., 85, 2149, 1963). The solid phase syntheses of peptides have commercialized the availability of large-scale (numbering several hundred thousands) peptide production. The success of these developments largely depended on the elimination of intermediates in the synthesis and substitution of a platform or solid support to attach each amino acid to; the resulting short peptide chains can be manufactured using resin beads, cotton, or plastic pins. Besides the above mentioned methods of producing the peptides, the peptides may also be produced by other conventional chemical synthetic methods, methods of producing a DNA correspond to the desired peptide and introducing the DNA into a suitable vector for production in animal cells or microorganisms to produce the desired peptides, or methods of chemically modifying the produced peptide in a suitable manner.

A wide variety of ways are available for introducing the B.t. gene expressing the toxin and associated fragments into the microorganism host under conditions which allow for stable maintenance and expression of the gene. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

These amino acid constituents can consist of L- or D-enantiomeric derivatives and modified peptide backbones such as peptoids and mimetics. Further since the relevant compounds derive from similar naturally occurring amino acid sequences, aqueous or lipophilic (e.g. octanol or acetone) isolation and purification can likewise support manufacture and pharmaceutical supply.

The amino acids (SEQ. I.D. No. 1–2) shown in Table I identify essential fragments to demonstrate preservative or antimicrobial efficacy, but are not limited by truncated or synthetic amino acid sequences which share at least in part or in whole the amino acid sequence shown in Tables I and II. Various analogs and derivatives can be predicted by those skilled in the art of peptide chemistry and computer modelling, but within the scope of the disclosure may be equivalent in biological function and structure. Examples of such derivatives are presented in Tables I–III. To manipulate the polypeptide sequence, standard methods including probing the importance of each amino acid by sequential alanine or glycine substitutions, examining sterically restricted cis- and trans-substitutions with the aromatic proline, and progressively shortening the amino (N—) terminus until antimicrobial potency diminishes quantitatively.

Table II shows the spectrum of preservative and antimicrobial effectiveness for synthetic peptides of the present invention against representative organisms and corresponding infectious ailments. Table III lists the minimum inhibitory concentration (ug/mL) for the various organisms assayed in Mueller-Hinton growth media. Details of the microbiological techniques employed are available to those skilled in the art, for instance from the American Type Tissue Culture Catalog (ATCC, Maryland) or DIFCO Manual, 10th Edition, 1984, pp. 78–80. For instance, a cultured solution of the bacterial strains *Escherichia coli* (American Tissue Culture Collection, Maryland) ATCC 259222 and *Pseudomonas aeruginosa* ATCC 27853 can be tested to model Gram-negative bacteria. Bacteria were grown overnight at 37 C. in Mueller-Hinton broth, reinoculated and incubated at 37 C. to reach the exponential phase of bacterial growth [i.e. a final bacterial suspension cantaining from 100,000 to 500,000 colony-forming units [(CFU)/ml]. In 96 well tissue culture plates, peptides dissolved in distilled water were added to the bacterial suspension at concentrations varying between 1000 to 2 ug/mL derived from serial dilutions, and then incubated overnight at 37 C. The 50% inhibitory concentration and minimum inhibitory concentration (MIC) were defined as the concentration of peptide at which there was 50% reduction in the optical density (absorbance, OD) and the concentration at which there was no change in optical density, between time 0 and 16 h at 620 nm using a multiscan plate reader.

Table III lists the approximate pharmacokinetics of synthetic peptides described in the present invention which solubilize readily, persist in conformationally active secondary structures in vivo, and induce lysis of representative bacteria, yeast and fungi. These determinations derive from optical density readings (O.D.) and rely on spectrophotometric absorbance from known initial concentrations as reference standards. The optimal therapeutic index for dosage and effective antimicrobial inhibition of a particular polypeptide or salt thereof range between 10–100 and follow routinely without elaborate laboratory determinations by those skilled in the art of pharmacokinetics and metabolic pathways using, for instance, various cytochrome and liver enzymes in vivo.

A combination of physical (heat) and chemical agents may be used to preserve and prolong the activity of the active fragment produced in the cell when the cell or a chemical fragment derived from the cell is administered to the host animal. Examples of physical means are short wavelength radiation such as gamma-radiation and X-radiation, freezing, UV irradiation, lyophilization, and the like.

One clear conclusion from tabulated data is that the polypeptides of the present invention display a broad spectrum of preservative and antimicrobial effectiveness, including favorable therapeutic indices as well as microcidal effects against gram positive and gram negative bacteria, strains of yeast and fungi and the like. Therefore, frequently encountered clinical conditions, such as pneumonia (e.g. streptococci), fungal skin infections and hospital iatrogenic ailments (e.g. Staph.), may receive the treatment and control methods of administering the polypeptides of the present invention to a host, organ or tissue in plant, animal, and human afflictions. For example, serious antibiotic resistant bacterial diseases known as hospital acquired infections has been rising at the same time there is an increasing number of infections that are essentially untreateable or difficult to treat. Infectious disease is currently the third most frequent cause of death in the U.S. In physiological or nutritional media, these antibiotic properties offer further sterilizing or preservative use for combining such antimicrobial action with other therapeutics in synergistic formulations.

To those skilled in the art of pharmaceutical formulation, the present invention serves as an active ingredient concentrated to deliver relief of clinical ailments using a generally regarded as safe (GRAS) carrier prepared using the results herein. This carrier comprises fillers, non-toxic buffers, physiological (phosphate buffered) saline, and various adjustable viscous creams or ointments (e.g. methyl cellulose thickeners). Acidic pH adjustment for physiological application further comprises addition of regulatory acids, bases and buffers, such as citric or acetic acid generally formulated but not limited to give a lower pH than neutral for peptide stability and lengthened half-lives. Suitable lypholized powders, liquids, or semi-solid forms include injectable compositions via catheter or syringe, oral tables or capsules, pastes, gums, ointments, patches and inhalable constituents. Co-administration of the described polypeptides can further be combined with proteinase inhibitors (such as trypsin or chymotrypsin inhibitors) and synergistic formulations designed to enhance the inhibitory potency of the present invention.

As a wettable antimicrobial or insecticidal peptide, the concentration will vary widely depending upon the nature of the particular formulation, particularly whether it is a concentrate or to be used directly. The antifungal pesticide will be present in at least 1% by weight and may be 100% by weight delivered as a wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiableconcentrates, or the like. The ingredients may include Theological agents,surfactants, emulsifiers, dispersants, or polymers. The dry formulations will have from about 1–95% by weight of the antifungal or pesticide while the liquid formulations will generally be from about 1–60% by weight of the solids in the liquid phase. The formulations will generally have from about 100 to about 10,000 cells/mg. These formulations will be administered at about 50 mg (liquid or dry) to 1 kg or more per hectare.

These detailed descriptions are understood as illustrative and subject to modification or change by those skilled in the art, thereby included within the purview and spirit of the appended claims.

Summary of the Antimicrobial Amino Acid Sequence Data

An object of this invention is to provide a short amino acid chain capable of inhibiting microbial growth and spoilage of an aqueous solution containing whole cells, membranes, and in vivo infectious agents. Novel antimicrobial peptides are described herein. The peptides comprise amino acid chains represented by the following single letter designations:

GIGTLLGKKKTKFLKNILKL  as represented in ID sequence No. 1

VGSLVGKRILSELRNLI  as represented in ID sequence No. 2

Definitions

The single-letter amino acid representation is used (i.e A=alanine; C=cysteine, D=aspartic acid; E=glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine).

The amino acid sequences of the present invention are also identified herein by their three letter amino acid representations. The convention for three-letter amino acid representations is as follows: Ala=alanine; Cys=cysteine; Asp=aspartic acid; Glu=glutamic acid; Phe=phenylalanine; Gly=glycine; His=histidine; Ile=isoleucine; Lys=lysine; Leu=leucine; Met=methionine; Asn=asparagine; Pro=proline; Gln=glutamine; Arg=arginine; Ser=serine; Thr=threonine; Val=valine; Trp=tryptophan; Tyr=tyrosine.

BRIEF DESCRIPTION OF THE INVENTION

TABLE 1: shows the primary sequence of the novel peptides.

TABLE 1

| Sequence I.D. | Endgroup (N terminus) | | | | | | | | | | | | | | | | | | | | Endgroup (C terminus) |
|---|---|---|---|---|---|---|---|---|---|---|---|---|---|---|---|---|---|---|---|---|---|
| 1 | (H-) | G | I | G | T | L | L | G | K | K | K | T | K | F | L | K | N | I | L | K | L | (Amide-) |
| 2 | (H-) | | V | G | S | L | V | G | K | R | I | L | S | E | L | R | N | L | I | | | (Aide-) |

TABLE 2: shows certain antimicrobial properties of the novel peptides.

TABLE 2

Minimum Inhibitory Concentration (MIC ug/mL)

| | Organism (ATCC) | MIC (ug/mL) | SEQ. ID 1 |
|---|---|---|---|
| Gram Negative Bacteria | E. coli(25922) | 16.00 | |
| | Ps. Aruginosa(13883) | 32.00 | |
| Gram Positive Bacteria | Staph aureus(25923) | 63.00 | |
| Yeasts | Sac.cerv. | 16.00 | |
| | Pichia | 8.00 | |

TABLE 3: shows the comparative in vivo pharmacokinetic properties of the novel peptides against infectious organisms.

TABLE 3

| Seq. I.D. | Molec. Weight | Solubility (ug/100 g) | Biostability Mammalian | Half-life Yeast | (hours) E. coli |
|---|---|---|---|---|---|
| 1 | 2513.31 | 85.09 | 30.00 | 20.00 | 10.00 |
| 2 | 1866.60 | 16.50 | 100.00 | 20.00 | 10.00 |

TABLE 4: shows the secondary structure of the novel peptides.

TABLE 4

| Seq. ID No.: | MW | isoelectric | charge at ph7 | 1 mg = nM | % charged | % acidic | % hydrophobic | % alpha | % beta | % turn |
|---|---|---|---|---|---|---|---|---|---|---|
| 1 | 2513.31 | 10.70 | 5.90 | 452.00 | 30.00 | 0.00 | 40.00 | 100.00 | 0.00 | 0.00 |
| 2 | 1866.60 | 10.89 | 1.91 | 535.00 | 23.53 | 5.88 | 47.06 | 29.41 | 70.59 | 0.00 |

DETAILED DESCRIPTION OF THE ANTIMICROBIAL CHEMICAL INNOVATIONS

In accordance with the present invention, there is provided a peptide having antimicrobial activity, the peptide consisting of an amino acid chain represented by:

```
Gly Ile Gly Thr Leu Leu Gly Lys Lys Lys
1               5                   10

Thr Lys Phe Leu Lys Asn Ile Leu Lys Leu
                15                  20
``` as set forth in SEQ ID. No. 1, or salts thereof;

```
Val Gly Ser Leu Val Gly Lys Arg Ile Leu
1               5                   10

Ser Glu Leu Arg Asn Leu Ile
                15          20
``` as set forth in SEQ. ID. No. 2, or salts thereof;

Secondary Structure Determination

The antimicrobial peptides (1–2) according to the present invention were subjected to a prediction method for determining their secondary structure as an alpha-helical or beta-sheet configuration using the Garnier-Robson and Chou-Fasman criteria (e.g. Chou, Biopolymers, 33:1405, 1993). This analysis as shown in Table IV. revealed a predominantly alpha-helical structure in (SEQ. I.D. 1) with an approximate 5.4 angstrom per turn distance between residues.

A number of structural advantages feature in SEQ. 1–2 in addition to the primary function of no longer requiring either long peptide manufacturing, toxic material handling and multiple gene family experssion for *B.t.* related proteins or precursors. Oral formulations generally depend on bioavailability in vivo which is often a function of molecular weight. The solubility for SEQ. 1, for example, is 5 times longer than the *B.t.* fragment SEQ. 2. Furthermore, the elimination of Ser-amino acids in the *B.t.* fragment SEQ. 2, which alone lacks antimicrobial action, renders SEQ. 1 resistant to beta-elimination reactions at basic pH with metals. Metal contamination in manufacturing or storage in vials with metal caps typically reduce shelf-life of peptides. The elimination of two Arg-amino acids on the *B.t.* protein fragment, SEQ. 2, which alone lacks antimicrobial action, renders SEQ. 1 less hydrophobic and thus partially accounts for the dramatic rise in solubility. It is clear that the fundamental peptide chemistry of SEQ. 1 renders improved stability to side-reactions for improved bioavailability while providing sub-micromolar antimicrobial potency.

These modifications become important since it has been found that many microbial agents are sensitive to environmental factors, *Bt* is extremely sensitive to sunlight; it has been found to be rendered 80% ineffective within one hour when exposed to direct sunlight. Other environmental factors influencing the efficacy of *Bt* include wind, high temperatures (*Bt* operates maximally in the field at 18–200 C.), and loss from rain wash. As a result, *Bt* deposits remain active for relatively short periods following application. This low persistence of *Bt* in the environment creates the need for repeat applications of the insecticide, which makes it a very costly form of control compared to chemical pesticides; their high persistence eliminates the need for costly reapplications. The persistence of the insecticide for different environmental conditions can be dealt with in the formulation of the insecticide by the addition of stickers, while the problem of UV light can be tackled in the formulation by the addition of protectants. Persistence can also be increased through the use of recombinant technology.

The action of alpha-helical peptides, in general, derives from their natural proclivity for forming ion channels across membrane bilayers, particularly for those peptides longer than 20 residues. Ion channels formed by shorter (8–12 residue) monomers span the membrane bilayer as head-to-tail dimers or larger self-aggregated units. For favorable ion channel formation the aggregated confirmation places the hydrophilic residues inward and the hydrophobic residues free to interact with the cell wall's phospholipid groups. To induce potent antibacterial activity, the ion channel therefore serves to neutralize the membrane potential, thus ceasing normal charge transfer. This mechanism differs from bacteriostatic chemicals which for example, inhibit protein or DNA synthesis and offers advantages for bacteriocidal applications where contact killing is important. The antimicrobial effect may also be augmented by modifying the side chain of a suitable amino acid residue or by replacing a specific amino acid residue by another amino acid. The above shows that the novel amino acid sequence of *B.t.* can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser E. T. and Kezdy, F. J. [1984] Science 223:249–255) Thus, the subject invention includes mutants of the amino acid sequence depicted herein which do not alter the protein secondary structure, or if the structure is altered, the biological activity is retained to some degree.

What is claimed is:

1. A polypeptide consisting of:

```
Gly Ile Gly Thr Leu Leu Gly Lys Lys Lys
1               5                   10

Thr Lys Phe Leu Lys Asn Ile Leu Lys Leu
                15                  20
``` set forth in SEQ. ID. No. 1, or salts thereof.

2. A polypeptide consisting of:

```
Val Gly Ser Leu Val Gly Lys Arg Ile Leu
1               5                   10

Ser Glu Leu Arg Asn Leu Ile
                15                  20
``` set forth in SEQ. ID. No. 2, or salts thereof.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 20 Amino Acids
        (B) TYPE: Amino Acid
        (D) TOPOLOGY: UNKNOWN (ii) MOLECULE TYPE: Peptide (xi) SEQUENCE DESCRIPTION: SEQ ID NO: 1:

```
Gly Ile Gly Thr Leu Leu Gly Lys Lys Lys
1               5                   10

Thr Lys Phe Leu Lys Asn Ile Leu Lys Leu
                15                  20
```

(2) INFORMATION FOR SEQ ID NO: 2:

(i) SEQUENCE CHARACTERISTICS:
        (A) LENGTH: 17 Amino Acids
        (B) TYPE: Amino Acid
        (D) TOPOLOGY: UNKNOWN (ii) MOLECULE TYPE: Peptide (xi) SEQUENCE DESCRIPTION: SEQ ID NO:2:

```
Val Gly Ser Leu Val Gly Lys Arg Ile Leu
1               5                   10

Ser Glu Leu Arg Asn Leu Ile
                15
```